United States Patent
Koester et al.

(10) Patent No.: US 8,552,311 B2
(45) Date of Patent: Oct. 8, 2013

(54) ELECTRICAL FEEDTHROUGH ASSEMBLY

(75) Inventors: Kurt J. Koester, Los Angeles, CA (US); Timothy Beerling, San Francisco, CA (US)

(73) Assignee: Advanced Bionics, Valencia, CA (US)

( * ) Notice: Subject to any disclaimer, the term of this patent is extended or adjusted under 35 U.S.C. 154(b) by 346 days.

(21) Appl. No.: 12/836,831

(22) Filed: Jul. 15, 2010

(65) Prior Publication Data
US 2012/0012374 A1 Jan. 19, 2012

(51) Int. Cl.
*H05K 1/00* (2006.01)
*H05K 13/00* (2006.01)

(52) U.S. Cl.
USPC ........... 174/262; 174/263; 174/264; 174/265; 174/266; 174/360; 174/650

(58) Field of Classification Search
USPC ......... 174/262–266, 650, 360, 258; 257/698, 257/E23.011, 182; 438/667
See application file for complete search history.

(56) References Cited

U.S. PATENT DOCUMENTS

| | | | | |
|---|---|---|---|---|
| 2,318,435 | A | * | 5/1943 | Stupakoff et al. ..... 174/152 GM |
| 3,063,144 | A | * | 11/1962 | Palmour, III ............... 228/124.1 |
| 3,065,533 | A | * | 11/1962 | Dungan et al. ................ 228/121 |
| 4,152,540 | A | * | 5/1979 | Duncan et al. ........ 174/152 GM |
| 4,217,137 | A | * | 8/1980 | Kraska et al. ................. 420/507 |
| 4,445,511 | A | | 5/1984 | Cowdery et al. |
| 4,700,881 | A | | 10/1987 | Ryan |
| 4,721,831 | A | | 1/1988 | Vora |
| 4,785,827 | A | | 11/1988 | Fischer |
| 4,837,230 | A | | 6/1989 | Chen et al. |
| 4,874,910 | A | | 10/1989 | McCoy |
| 5,085,720 | A | | 2/1992 | Mikeska et al. |
| 5,254,191 | A | | 10/1993 | Mikeska et al. |
| 5,282,841 | A | | 2/1994 | Szyszkowski |
| 5,304,517 | A | | 4/1994 | Casey et al. |
| 5,315,239 | A | | 5/1994 | Vitriol |
| 5,333,095 | A | * | 7/1994 | Stevenson et al. ............ 361/302 |
| 5,336,246 | A | | 8/1994 | Dantanarayana |
| 5,440,802 | A | | 8/1995 | Whitney et al. |
| 5,474,741 | A | | 12/1995 | Mikeska et al. |
| 5,474,834 | A | | 12/1995 | Tanahashi et al. |
| 5,513,793 | A | | 5/1996 | Malmgren |

(Continued)

FOREIGN PATENT DOCUMENTS

| | | |
|---|---|---|
| EP | 0660449 A2 | 6/1995 |
| EP | 0660449 A3 | 6/1995 |

(Continued)

OTHER PUBLICATIONS

Adtech Ceramics, Design & Capabilities Guide, Ceramic Packages-Chemical Milling-Injection Molding, Advanced Technical Ceramics Company 2007.

(Continued)

*Primary Examiner* — Anatoly Vortman
(74) *Attorney, Agent, or Firm* — Steven L. Nichols; Van Cott, Bagley, Cornwall & McCarthy P.C.

(57) ABSTRACT

An electrical feedthrough includes a ceramic body and a ribbon via extending through the ceramic body, an interface between the ribbon via and the ceramic body being sealed using partial transient liquid phase bonding. The ribbon via extends out of the ceramic body and makes an electrical connection with an external device.

23 Claims, 12 Drawing Sheets

(56) References Cited

U.S. PATENT DOCUMENTS

| | | | |
|---|---|---|---|
| 5,591,287 A | 1/1997 | Clegg et al. | |
| 5,620,476 A | 4/1997 | Truex et al. | |
| 5,683,435 A | 11/1997 | Truex et al. | |
| 5,738,270 A | 4/1998 | Malmgren | |
| 5,750,926 A | 5/1998 | Schulman et al. | |
| 5,825,608 A * | 10/1998 | Duva et al. | 361/302 |
| 5,847,453 A * | 12/1998 | Uematsu et al. | 257/728 |
| 5,855,995 A | 1/1999 | Haq et al. | |
| 5,937,321 A | 8/1999 | Beck et al. | |
| 6,008,980 A | 12/1999 | Stevenson et al. | |
| 6,011,993 A * | 1/2000 | Tziviskos et al. | 607/36 |
| 6,041,496 A | 3/2000 | Haq et al. | |
| 6,066,808 A * | 5/2000 | Kresge et al. | 174/262 |
| 6,139,666 A | 10/2000 | Fasano et al. | |
| 6,146,743 A | 11/2000 | Haq et al. | |
| 6,205,032 B1 | 3/2001 | Shepherd | |
| 6,275,369 B1 * | 8/2001 | Stevenson et al. | 361/302 |
| 6,284,080 B1 | 9/2001 | Haq et al. | |
| 6,411,854 B1 * | 6/2002 | Tziviskos et al. | 607/57 |
| 6,414,835 B1 | 7/2002 | Wolf et al. | |
| 6,424,234 B1 * | 7/2002 | Stevenson | 333/182 |
| 6,516,808 B2 | 2/2003 | Schulman | |
| 6,548,011 B1 | 4/2003 | Rhee et al. | |
| 6,554,178 B1 | 4/2003 | Tsukamoto | |
| 6,560,860 B2 | 5/2003 | Shepherd | |
| 6,660,116 B2 | 12/2003 | Wolf et al. | |
| 6,863,450 B2 | 3/2005 | Mazotti et al. | |
| 6,989,200 B2 | 1/2006 | Byers et al. | |
| 7,068,491 B1 | 6/2006 | Burdon et al. | |
| 7,073,961 B2 | 7/2006 | Mazotti et al. | |
| 7,107,855 B2 * | 9/2006 | Bjoerkman | 73/724 |
| 7,127,286 B2 | 10/2006 | Mech et al. | |
| 7,142,909 B2 | 11/2006 | Greenberg et al. | |
| 7,164,572 B1 | 1/2007 | Burdon et al. | |
| 7,174,223 B2 | 2/2007 | Dalton et al. | |
| 7,190,051 B2 | 3/2007 | Mech et al. | |
| 7,211,103 B2 | 5/2007 | Greenberg et al. | |
| 7,211,510 B2 | 5/2007 | Meadows | |
| 7,257,446 B2 | 8/2007 | Greenberg et al. | |
| 7,291,540 B2 | 11/2007 | Mech et al. | |
| 7,341,802 B1 | 3/2008 | Ota et al. | |
| 7,480,988 B2 | 1/2009 | Ok et al. | |
| 7,497,846 B2 | 3/2009 | Uhland et al. | |
| 7,524,535 B2 | 4/2009 | Kim et al. | |
| 7,818,876 B2 | 10/2010 | Suaning | |
| 7,901,761 B1 | 3/2011 | Jiang et al. | |
| 7,988,507 B2 | 8/2011 | Darley et al. | |
| 7,996,982 B2 | 8/2011 | Darley et al. | |
| 8,277,227 B2 | 10/2012 | Darley et al. | |
| 2002/0139556 A1 | 10/2002 | Ok et al. | |
| 2003/0109903 A1 | 6/2003 | Berrang et al. | |
| 2004/0012942 A1 * | 1/2004 | Bjoerkman et al. | 361/807 |
| 2004/0093038 A1 | 5/2004 | Biggs et al. | |
| 2005/0247475 A1 | 11/2005 | Stevenson et al. | |
| 2005/0288733 A1 | 12/2005 | Greenberg et al. | |
| 2006/0071056 A1 * | 4/2006 | Das | 228/245 |
| 2006/0186473 A1 | 8/2006 | Mech et al. | |
| 2006/0283624 A1 | 12/2006 | Ok et al. | |
| 2007/0005112 A1 | 1/2007 | Greenberg et al. | |
| 2007/0013014 A1 * | 1/2007 | Guo et al. | 257/417 |
| 2007/0021787 A1 | 1/2007 | Greenberg et al. | |
| 2007/0041164 A1 | 2/2007 | Greenberg et al. | |
| 2007/0060969 A1 | 3/2007 | Burdon et al. | |
| 2007/0060970 A1 | 3/2007 | Burdon et al. | |
| 2007/0096281 A1 | 5/2007 | Greenberg et al. | |
| 2007/0112396 A1 | 5/2007 | Dalton et al. | |
| 2007/0207569 A1 | 9/2007 | Greenberg et al. | |
| 2007/0236861 A1 | 10/2007 | Burdon et al. | |
| 2007/0277374 A1 | 12/2007 | Suaning | |
| 2008/0027515 A1 | 1/2008 | Harris et al. | |
| 2008/0046021 A1 | 2/2008 | Greenberg et al. | |
| 2008/0053638 A1 | 3/2008 | Appleby et al. | |
| 2008/0060834 A1 | 3/2008 | Eck et al. | |
| 2008/0077195 A1 | 3/2008 | Greenberg et al. | |
| 2008/0208289 A1 | 8/2008 | Darley et al. | |
| 2008/0209723 A1 | 9/2008 | Darley et al. | |
| 2008/0217784 A1 | 9/2008 | Binder et al. | |
| 2009/0034769 A1 | 2/2009 | Darley et al. | |
| 2009/0124965 A1 | 5/2009 | Greenberg et al. | |
| 2010/0019985 A1 | 1/2010 | Bashyam et al. | |
| 2010/0292760 A1 | 11/2010 | Leigh et al. | |
| 2011/0000699 A1 | 1/2011 | Bealka et al. | |
| 2011/0139484 A1 * | 6/2011 | Koester et al. | 174/50.56 |
| 2012/0016444 A1 * | 1/2012 | Koester | 607/57 |

FOREIGN PATENT DOCUMENTS

| | | |
|---|---|---|
| EP | 0441528 B1 | 10/1996 |
| EP | 0844899 B1 | 7/2003 |
| EP | 1547207 B1 | 8/2011 |
| GB | 2134335 | 8/1984 |
| JP | 59111868 A2 | 6/1984 |
| JP | 60211345 A2 | 4/1985 |
| JP | 61145526 | 7/1986 |
| JP | 6356378 A2 | 6/1988 |
| JP | 63156378 A2 | 6/1988 |
| JP | 01-294061 | 11/1989 |
| JP | 04023303 A2 | 1/1992 |
| JP | 06061611 A | 3/1994 |
| JP | 06218872 | 8/1994 |
| JP | 07-211851 | 8/1995 |
| JP | 09147710 A | 6/1997 |
| JP | 10126119 A2 | 5/1998 |
| JP | 10194856 A | 7/1998 |
| JP | 11224984 A | 8/1999 |
| JP | 2001-284774 | 10/2001 |
| JP | 2002368422 A2 | 12/2002 |
| JP | 2004-119587 | 4/2004 |
| JP | 2006032439 A2 | 2/2006 |
| JP | 2009246391 A2 | 10/2009 |
| WO | 89/07834 | 8/1989 |
| WO | 94/08539 | 4/1994 |
| WO | 97/06853 | 2/1997 |
| WO | 2004/030159 | 4/2004 |
| WO | 2007/070989 | 6/2007 |
| WO | 2009/003235 | 1/2009 |
| WO | 2009/009827 | 1/2009 |

OTHER PUBLICATIONS

Shalz et al., Ceramic Joining Part I Partial transient liquid-phase bonding of alumina via Cu/Pt interlayers. Journal of Materials Science 28 (1993) 1673-1684.

Shalz et al., Ceramic Joining II Partial transient liquid-phase bonding of alumina via Cu/Ni/Cu multilayer interlayers, Journal of Materials Science 29 (1994) 3200-3208.

Shalz et al., Ceramic Joining III Bonding of alumina via Cu/Nb/Cu interlayers, Journal of Materials Science 29 (1994) 3678-3690.

Sugar et al, Ceramic joining IV. effects of processing conditions on the properties of alumina joined via Cu/Nb/Cu interlayers, Journal of Materials Science 36 (2001) 5609-5624.

Sugar et al, Liquid-Film-Assisted Formation of Alumina/Niobium Interfaces, Journal of the American Ceramic Society, vol. 85 Issue 10, pp. 2523-2530, Published Online: May 10, 2005.

MacDonald et al, Transient Liquid Phase Bonding, to microelectronics and MEMS packaging, Department of Materials Science and Engineering, Massachusetts Institute of Technology, Cambridge, Massachusetts 02139 , 1992.

Platinum Foil in Ceramic Bonding, Platinum Metals Review, vol. 37 Jul. 1993, http://www.platinummetalsreview.com/pdf/pmr-v37-i3-130-184.pdf.

Kurt J. Koester; "Implantable Hermetic Feedthrough"; U.S. Appl. No. 12/836,899, filed Jul. 15, 2010.

Kurt J. Koester; "Particulate Toughened Ceramic Feedthrough"; U.S. Appl. No. 61/423,355, filed Dec. 15, 2010.

Rodel et al; Ceramic/Metal Interfacial Crack Growth:Toughening by Controlled Microcracks and Interfacial Geometries; Acta metall. vol. 36, No. 8, pp. 2083-2093, 1988.

* cited by examiner

ELECTRICAL FEEDTHROUGH ASSEMBLY

BACKGROUND

A variety of implanted medical devices can be used to extend and improve the life of a patient. These implanted medical devices often include electronics that monitor internal and external parameters and control the application of various therapies. To prevent body fluids from damaging electronic components that may be present within the device, the circuitry included with the internal unit is often enclosed within a hermetically sealed case. An electrical feedthrough may be used to transfer signals from the circuitry inside the hermetic case to the exterior of the case and vice versa. This electrical feedthrough maintains the integrity of the hermetic case, while allowing electrical signals to pass through.

One example of an implanted medical device is a cochlear implant. Cochlear implants include a hermetically sealed internal processor that receives and transmits electrical signals through a hermetic feedthrough. The internal processor receives electrical signals, which represent environmental sounds. The internal processor conditions these signals and selectively activates electrodes in the patient's cochlea to provide the patient with a sense of hearing. The electrical feedthrough in the hermetic housing should meet a number of rigorous requirements, including having an extremely small size, maintaining a gas and liquid seal over the patient's lifetime, mechanical reliability, providing a low electrical resistance connection between internal and external components, biocompatibility, and other requirements.

BRIEF DESCRIPTION OF THE DRAWINGS

The accompanying drawings illustrate various embodiments of the principles described herein and are a part of the specification. The illustrated embodiments are merely examples and do not limit the scope of the claims.

Throughout the drawings, identical reference numbers designate similar, but not necessarily identical, elements.

DETAILED DESCRIPTION

As mentioned above, a cochlear implant may be used to partially restore hearing in a patient by directly stimulating nerve cells. One component of the cochlear implant is an internal processor, which is typically implanted underneath the skin above the ear. The internal processor receives signals from an exterior unit and transfers those signals into electrical impulses. These electrical impulses travel along wires that run from the internal unit to electrodes, which directly stimulate the cochlea.

To prevent bodily fluids from damaging electronic components within the device, the circuitry included with the internal unit is enclosed within a hermetically sealed enclosure. An electrical feedthrough may be used to transfer signals from the circuitry inside the hermetic enclosure to the exterior of the case and vice versa. This electrical feedthrough maintains the integrity of the hermetic enclosure, while allowing electrical signals to pass through.

To increase comfort and ease of implantation, as well as minimize surgical trauma, it is desirable that the cochlear implant be as small as possible. Depending on the design, reducing the size of the implant may also reduce the risk of damage to the implant from blows or impacts. However, reducing the size of the implant has the associated challenge of shrinking the size of the hermetic feedthroughs. Each hermetic feedthrough design has manufacturing and material limitations on how much it can be scaled down, i.e., there are limitations imposed by the fabrication method, structure, leak path, etc. of the feedthrough. The present specification describes an electrical feedthrough assembly that provides superior sealing, a small footprint, and a flexible design.

In the following description, for purposes of explanation, numerous specific details are set forth in order to provide a thorough understanding of the present systems and methods. It will be apparent, however, to one skilled in the art that the present apparatus, systems, and methods may be practiced without these specific details. Reference in the specification to "an embodiment," "an example," or similar language means that a particular feature, structure, or characteristic described in connection with the embodiment or example is included in at least that one embodiment, but not necessarily in other embodiments. The various instances of the phrase "in one embodiment" or similar phrases in various places in the specification are not necessarily all referring to the same embodiment.

Figure 1:
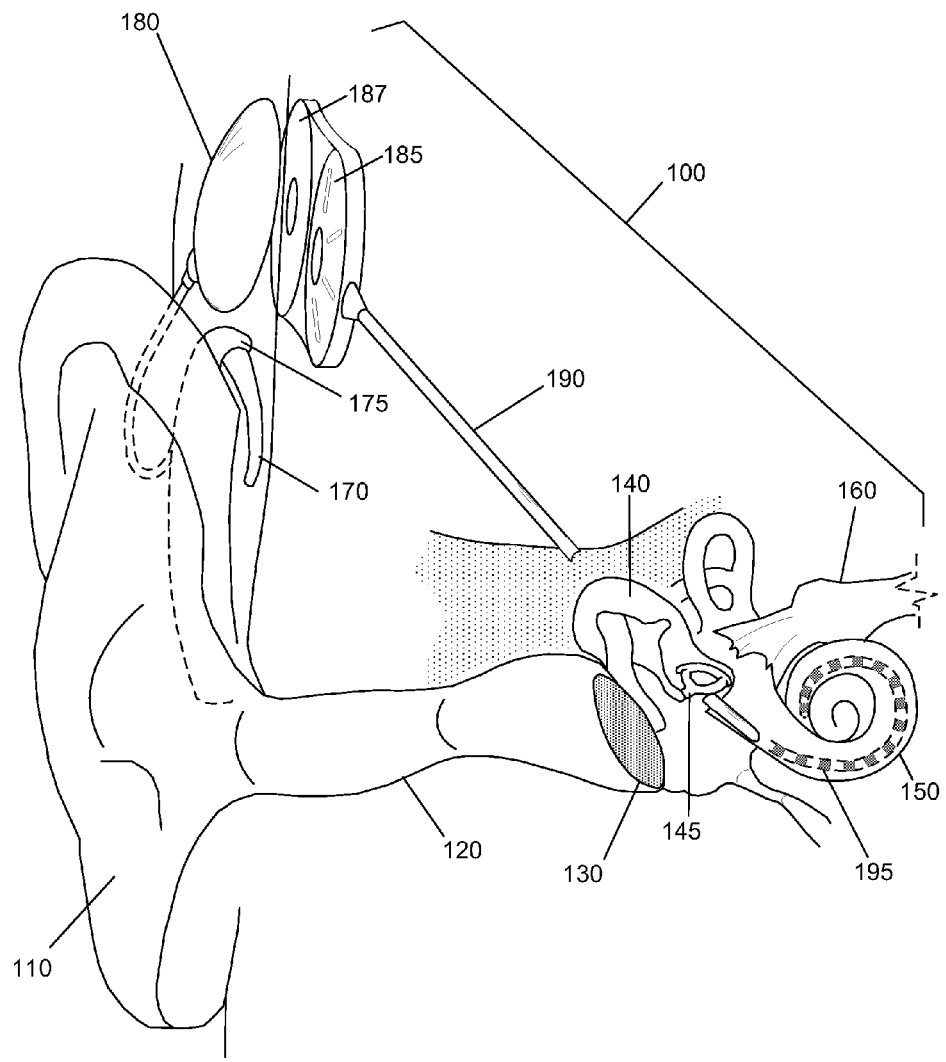
FIG. 1 is a diagram showing an illustrative cochlear implant system, according to one embodiment of principles described herein.

Referring now to the figures, FIG. 1 is a diagram showing one illustrative embodiment of a cochlear implant (100) surgically placed within the patient's auditory system. Ordinarily, sound enters the outer ear (110) and is directed into the auditory canal (120) where the sound wave vibrates the tympanic membrane (130). The motion of the tympanic membrane is amplified and transmitted through the ossicular chain (140), which consists of three bones in the middle ear. The third of the ossicles, or stirrup (145), contacts the outer surface of the cochlea (150) and causes movement of the fluid within the cochlea (150). Cochlear hair cells respond to the fluid-borne vibration in the cochlea (150) and trigger neural electrical signals that are conducted from the cochlea (150) to the auditory cortex by the auditory nerve (160).

As indicated above, the cochlear implant (100) is a surgically implanted electronic device that provides a sense of sound to a person who is profoundly deaf or severely hard of hearing. In many cases, deafness is caused by the absence or destruction of the hair cells in the cochlea, i.e., sensorineural hearing loss. In the absence of properly functioning hair cells, there is no way auditory nerve impulses can be directly generated from ambient sound. Thus, conventional hearing aids, which amplify external sound waves, provide no benefit to persons suffering from complete sensorineural hearing loss.

Unlike hearing aids, the cochlear implant (100) does not amplify sound, but works by directly stimulating the auditory nerve (160) with electrical impulses. Consequently, providing a cochlear prosthesis typically involves the implantation of electrodes into the cochlea. The cochlear prosthesis operates by direct electrical stimulation of the auditory nerve cells, bypassing the defective cochlear hair cells that normally traduce acoustic energy into electrical energy.

External components of the cochlear implant include a microphone (170), speech processor (175), and transmitter (180). The microphone (170) picks up sound from the environment and converts it into electrical impulses. The speech processor (175) selectively filters and manipulates the electrical impulses and sends the processed electrical signals through a cable to the transmitter (180). The transmitter (180) receives the processed electrical signals from the processor (175) and transmits them to the cochlear implant (100) by electromagnetic induction and/or by using radio frequencies.

The cochlear implant (100) may include an antenna (187) and an internal processor (185). The antenna (187) and internal processor (185) are secured beneath the user's skin, typically above and behind the external ear (110). The internal processor (185) includes electronic circuitry housed in a hermetically sealed enclosure. This electronic circuitry is connected via a hermetically sealed feedthrough to the antenna (187). The antenna (187) receives power and signals from the transmitter (180) via electromagnetic induction and/or radio frequency signals. The internal processor (185) processes the received signals and sends modified signals through a hermetic feedthrough to cochlear lead (190) and electrodes (195). The electrodes (195) are inserted into the cochlea (150) and provide electrical stimulation to the auditory nerve (160).

The implant works by using the tonotopic organization of the cochlea. The cochlea is arranged tonotopically, also referred to as "frequency-to-place" mapping. The tonotopic structure of the cochlea enables human beings to hear a broad range of acoustic frequencies. The nerve cells sense progressively lower frequencies from the basal end of the cochlea to the apex. For normal hearing, the brain is presented with the electrical signals from the different regions of the cochlea and, because of the tonotopic configuration of the cochlea, is able to discern the acoustic frequencies being heard. A cochlear implant simulates with its electrode contacts along the length of the cochlea to mimic this process.

Figure 2:
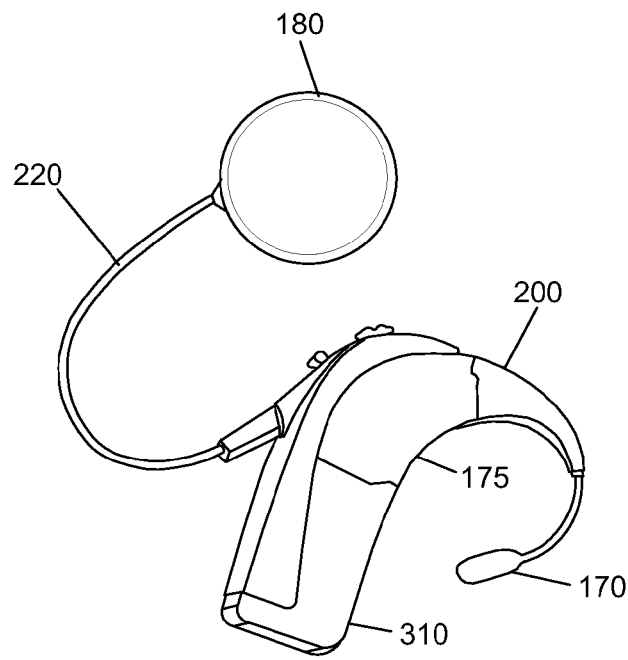
FIG. 2 is a diagram showing the external components of an illustrative cochlear implant system, according to one embodiment of principles described herein.

FIG. 2 shows one illustrative embodiment of the external components of the cochlear implant. The microphone (170) is attached to the ear hook (200). The ear hook (200) secures the external components behind the outer ear. The microphone (170) senses environmental sounds and converts those sounds into electrical impulses. The processor (175) filters and manipulates the electrical impulses it receives from the microphone (170) and transmits processed electrical sound signals along the external cable (220) to the transmitter (180). The processor (175), microphone (170) and transmitter (180) are powered by a battery (310).

Figure 3:
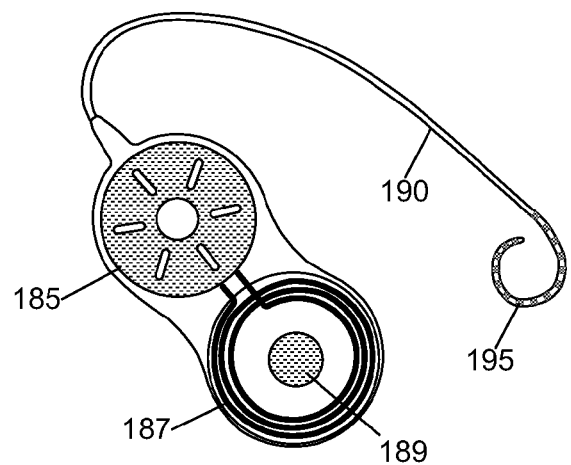
FIG. 3 is a diagram showing implanted components of an illustrative cochlear implant system, according to one embodiment of principles described herein.

FIG. 3 shows one illustrative embodiment of the internal components of the cochlear implant device. As described above, the antenna (187) is connected to the internal processor (185). According to one embodiment, the antenna (187) is a coiled wire or wires that are encapsulated by a silicone overmold. A cavity within the center portion of the antenna (187) is adapted to receive a magnet (189). The transmitter (180, FIG. 2) is held in place over the antenna (187) by magnetic interaction between components within the transmitter (180) and the implanted antenna magnet (189). The internal processor (185) is electrically connected to antenna (187) and receives signals and power via the antenna (187). The internal processor (185) is connected to the cochlear lead (190) which terminates in a flexible end that contains the electrodes (195). The electrodes (195) consist of a plurality of individual electrodes contacts made from platinum or a similar inert conductive material. These electrodes and associated wires are supported and connected by a flexible and durable biocompatible material, typically silicone rubber.

Figure 4A:
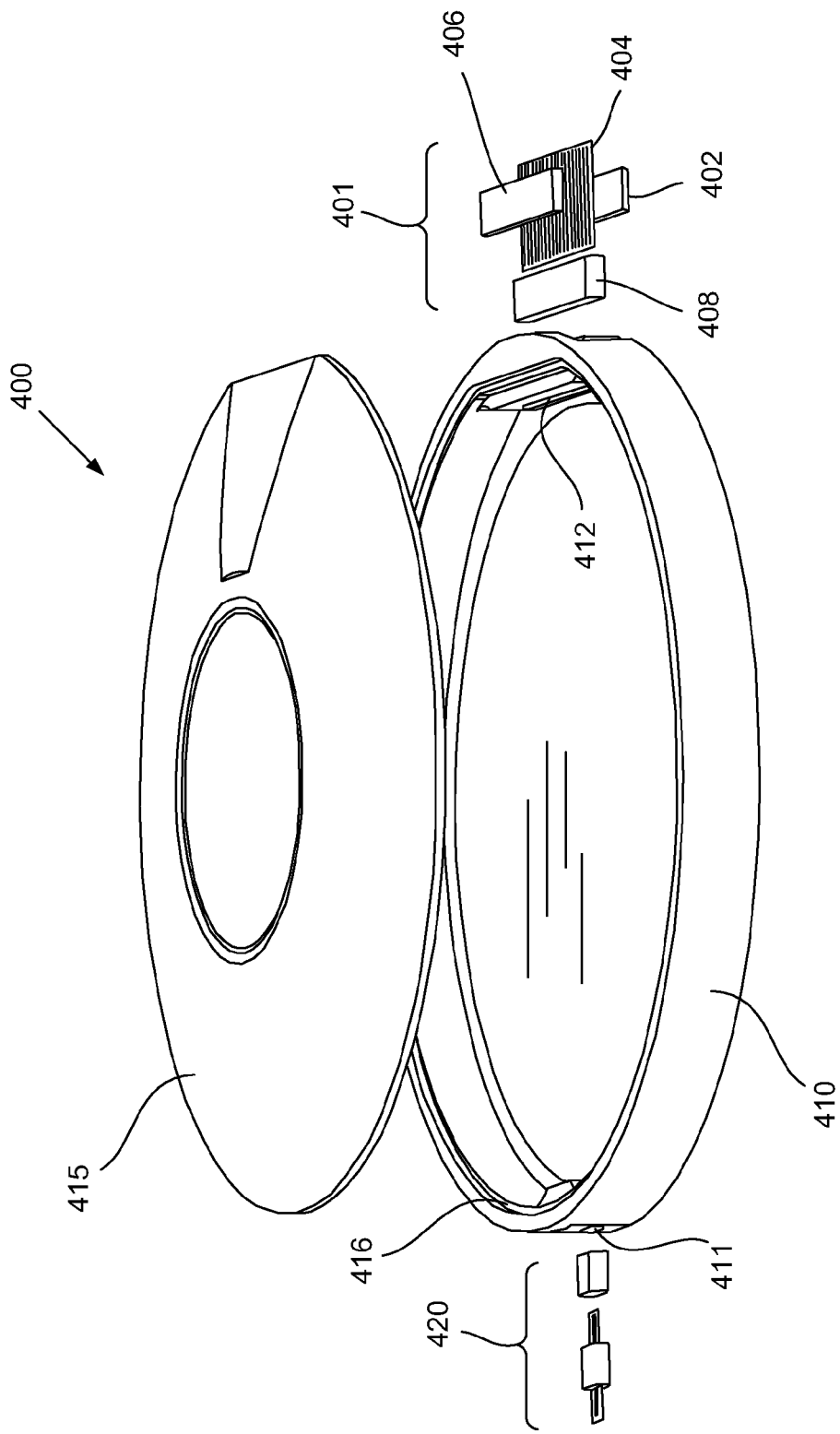
FIG. 4A is an exploded view of an illustrative hermetic enclosure that houses cochlear implant electronics, according to one embodiment of principles described herein.

FIG. 4A is an exploded view of an illustrative hermetic enclosure (400) that houses cochlear implant electronics. In this particular embodiment, the hermetic enclosure (400) includes a case (410) and a case top (415). The case (410) and the case top (415) may be formed from a variety of biocompatible materials. According to one illustrative embodiment, the case (410) and the case top (415) are formed from titanium. The case (410) shown in FIG. 4A is a closed bottom cylinder which is machined, stamped, or otherwise formed from a single piece of titanium. The case (410) includes two apertures which are configured to receive hermetic electrical feedthroughs (401, 420). The case top (415) is also made from titanium and can be placed onto a ledge (416) machined into the upper rim of the case (410). The case top (415) can then be laser welded onto the case (410). Once the case top (415) and hermetic electrical feedthroughs (401, 420) are in place, the hermetic enclosure (400) prevents liquids or gasses from entering the interior of the enclosure (400). As discussed above this prevents damage to electronics or other components housed in the interior of the hermetic enclosure (400).

According to one illustrative embodiment, the electrical hermetic feedthroughs (401, 420) are formed from a set of ribbon vias (404), which are sandwiched between a top ceramic layer (406) and a bottom ceramic layer (402). As discussed below, the top ceramic layer (406) and the bottom ceramic layer (402) are joined to form a monolithic ceramic body. The ribbon vias (404) pass through the monolithic ceramic body and are sealed in the ceramic body. The ceramic body is then joined to the aperture in the case (410). In this illustrative embodiment, a braze joint (408) is illustrated as joining the ceramic body to the case (410).

In this illustrative embodiment, the hermetic feedthroughs (401, 420) are on the perimeter of the case (410). In the example shown in FIG. 4A, the larger hermetic feedthrough (401) provides electrical connections between the electrodes in the cochlear lead and the internal electronics housed in the case. The smaller hermetic feedthrough (420) makes electrical connections between the antenna and the internal electronics. The hermetic feedthroughs (401, 420) are well protected by the case (410) to minimize damage from impact loads. Locating the feedthroughs around the perimeter of the case (410) can have a number of advantages, including a reduction in the overall height of the implanted device, simplifying manufacturing, and increased design flexibility in creating connectorized electrical interfaces between the internal electronics and the cochlear electrode. According to one illustrative embodiment, the overall height of the hermetic feedthrough (401) may be less than 2.5 mm. In other embodiments, the height of the hermetic feedthrough may on the order of 0.8 mm and 1.5 mm.

However, the hermetic feedthroughs (401, 420) could also be in other locations on the case (410) or the case top (415). Further, the number and size of hermetic feedthroughs (401, 420) could be varied according to the design requirements. For example, a single feedthrough could be used to interface all electrical connections to the internal electronics.

Figure 4B:
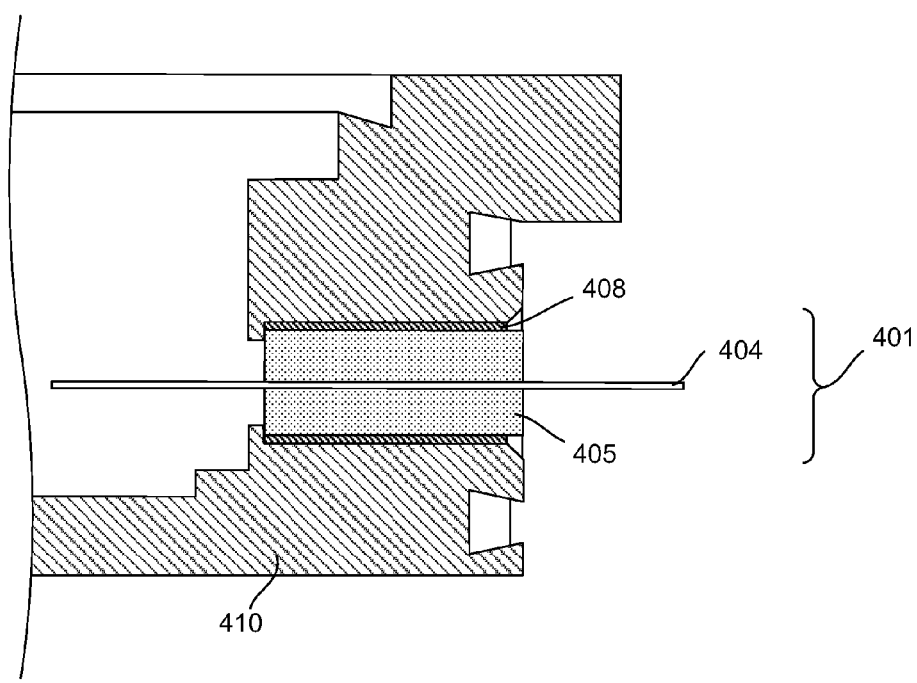
FIG. 4B is a cross sectional diagram of an illustrative hermetic case which includes a hermetic electrical feedthrough, according to one embodiment of principles described herein.

FIG. 4B is a cross sectional diagram of an illustrative hermetic case (410) with a hermetic electrical feedthrough (401). This figure shows ribbon vias (404) passing through the ceramic body (405) and extending from both sides of the ceramic body (405). The braze joint (408) seals the ceramic body (405) to the case (410). As discussed above, the case (410) may be formed from any biocompatible material which has the desired impermeability and mechanical characteristics. For example, titanium may be used to form the case. Titanium has a number of desirable characteristics, including high strength, resiliency, biocompatibility, low density, and low permeability.

The ceramic body (405) may be formed from a variety of materials. For example, the ceramic body (405) may be formed from alumina. The ribbon vias (404) may also be formed from a range of materials which have the desired characteristics. For example, the ribbon vias (404) may be formed from platinum. Platinum has a number of desirable characteristics, including a relatively low electrical resistance, high malleability, biocompatibility, and ability to be alloyed with a number of other elements.

The ceramic body (405) can be joined to the case in a number of ways, including brazing, active metal brazing, ceramic/glass/metal joining, transient liquid phase bonding, or other suitable techniques. According to one illustrative embodiment, a gold or gold alloy braze material is used to form a braze joint (408) which hermetically seals the feedthrough (401) into the case (410).

Figure 5A:
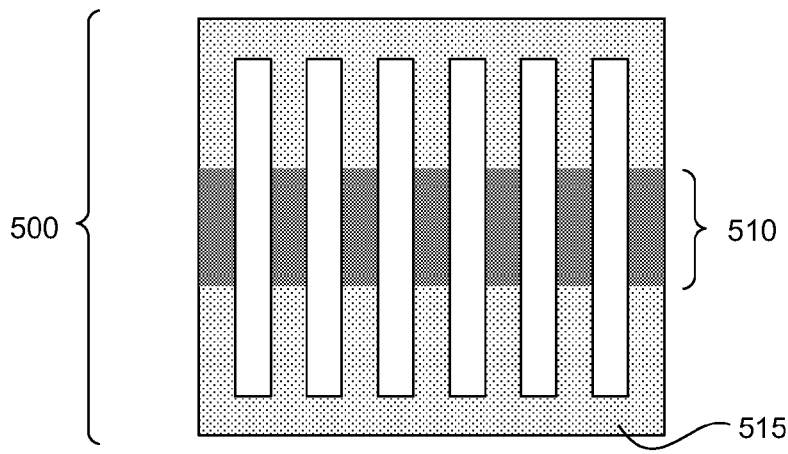
FIGS. 5A-5E are diagrams that show various illustrative steps in forming a hermetic electrical feedthrough, according to one embodiment of principles described herein.
Figure 5B:
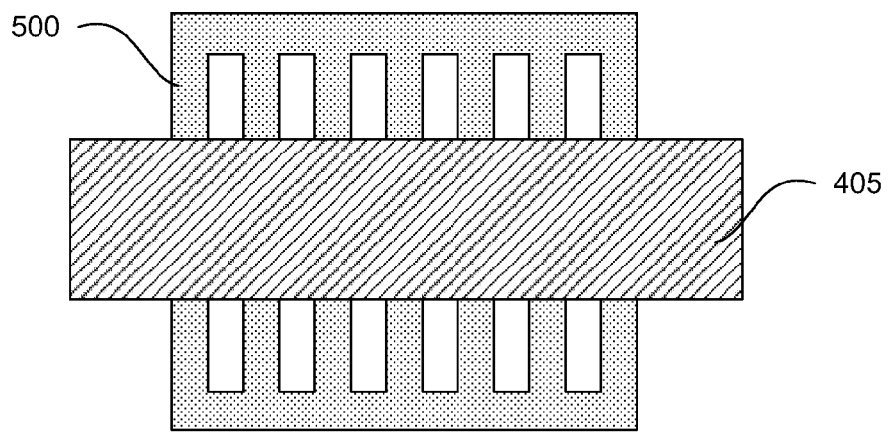
Figure 5C:
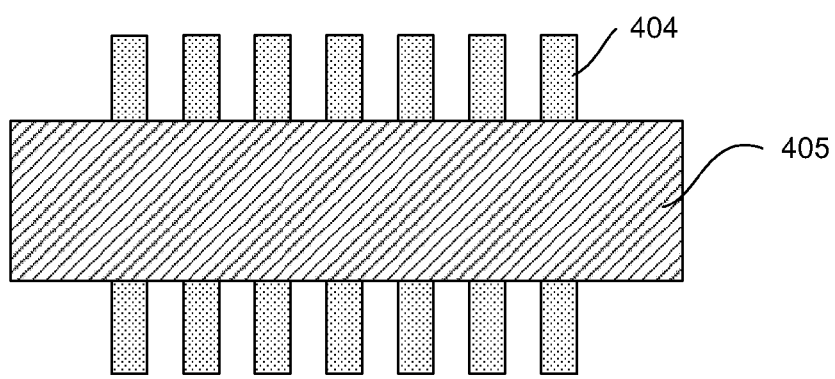

FIGS. 5A-5C are diagrams which show various illustrative steps in forming a hermetic electrical feedthrough. FIG. 5A shows a platinum frame (500). According to one illustrative embodiment, the platinum frame (500) is formed by stamping or micro-machining a sheet of platinum foil to form a number of discretized ribbon vias (404), which are joined together by a number of tethers (515). This micro-machining can be performed in a variety of ways, including short pulse laser machining. Short pulse laser micro-machining is defined as employing lasers with individual pulsewidths of less than one nanosecond, in order to minimize unwanted thermal effects when machining high thermal conductivity materials. The foil may have a thickness that is less than about 100 microns. In one illustrative embodiment, the platinum foil has a thickness between 25 and 30 microns. The individual ribbons may have a variety of widths and geometries. For example, the width of a ribbon may be between 0.005 inches and 0.012 inches. These ribbon vias (404) may have a number of advantages over vias that are created using platinum/glass inks, including lower electrical resistances. The lower electrical resistances of the ribbon vias (404) can significantly increase the power efficiency and battery life of a cochlear implant or other device.

In some embodiments, such as shown in FIG. 5A, a niobium or other layer (510) may be deposited on at least a portion of the platinum frame (500). In the example shown in FIG. 5A, a stripe of niobium is deposited across the center portion of the platinum frame (500). In other embodiments, the entire platinum frame (500) may be coated with a layer of niobium or may be deposited in various patterns over the frame surfaces. The niobium layer (510) may be on one side or both sides of the platinum frame (500). Additionally, the niobium layer (510) may be deposited before or after the micro-machining of the platinum frame (500). The niobium may be deposited onto the platinum frame (500) using a variety of techniques, including chemical vapor deposition, plasma enhanced chemical vapor deposition, evaporative deposition, sputtering, pulsed laser deposition, plating, or other deposition techniques. The niobium layer may have a range of thicknesses. For example, the niobium layer may be between 1 and 6 microns in thickness. In some illustrative embodiments, the niobium layer may be a separate niobium foil that is applied to either the platinum frame (500) or the ceramic and then joined with the platinum frame (500) during processing.

FIG. 5B shows a ceramic body (405), which covers the platinum frame (500). According to one illustrative embodiment, the ceramic body (405) is formed by laying out a first layer of green ceramic tape (402, FIG. 4A), placing the platinum frame (500) on the green ceramic tape, and then placing another green ceramic tape (406, FIG. 4A) over the platinum frame (500). This sandwiches the platinum frame (500) between the two green ceramic tapes. The green ceramic tapes are then pressed together and sintered into the monolithic ceramic body (405) with the platinum frame (500) embedded in the ceramic body (405) and extending out both sides of the ceramic body (405).

FIG. 5C shows the ceramic body (405) with the embedded platinum frame (500, FIG. 5B) which has been trimmed to remove the tethers and create separate ribbon vias (404). These ribbon vias (404) form individual conductive paths through the ceramic body (405) and can be used to conduct electrical signals through the ceramic body (405). The ribbon vias (404) overhang the dielectric ceramic body (405) on both sides to facilitate attachment of internal and external electrical components. As illustrated in FIGS. 4A and 4B, the ceramic body (405) can be joined to a hermetic case (410, FIG. 4B) to form a hermetic feedthrough (401, FIG. 4B), which allows electrical signals to pass into and out of the case (410, FIG. 4B) while preventing liquid or vapor from entering the case (410, FIG. 4B).

Figure 5D:
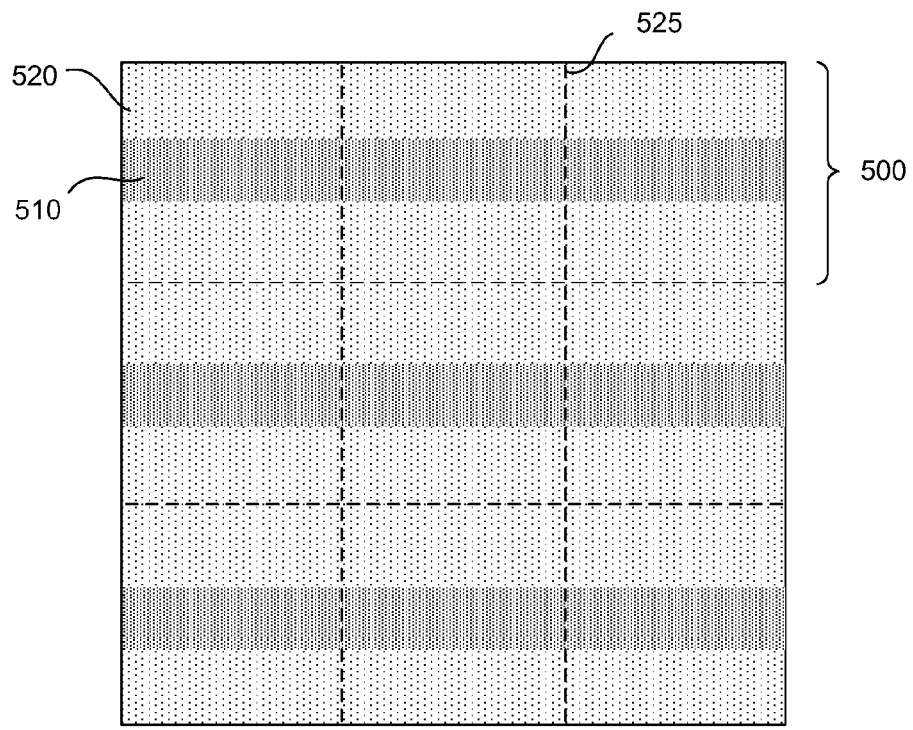

FIG. 5D shows a large platinum foil (520) on which a patterned niobium layer (510) has been deposited. As discussed above, this patterned niobium layer (510) may be deposited on one or both sides of the platinum foil (520). The dividing lines (525) show where the platinum foil (520) will be ultimately divided into a number of platinum frames (500). As shown in FIG. 5D, the platinum foil (520) will be divided into nine platinum frames (500). Each platinum frame (500) can be utilized to form ribbon vias in a ceramic feedthrough as described in FIGS. 5A-5C. The platinum foil (520) may have a variety of sizes, including sizes which are significantly larger that the platinum foil illustrated in FIG. 5D. For example, the platinum foil (520) may be sized to include tens or hundreds of platinum frames (500). By producing a large number of platinum frames (500) from a single platinum foil (520), the time and cost to manufacture platinum frames can be reduced.

Figure 5E:
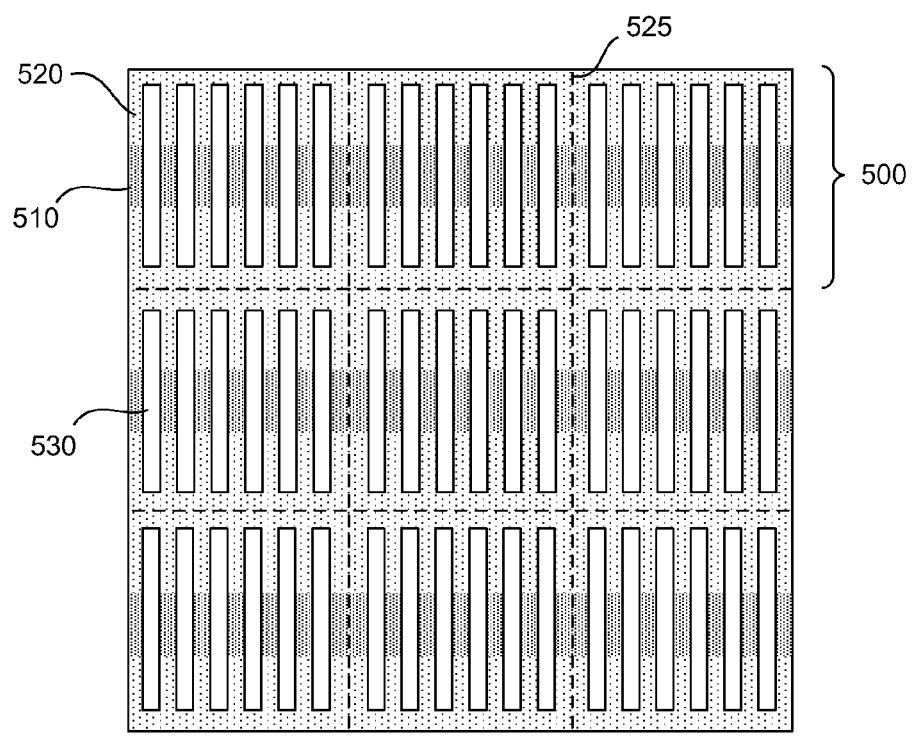

FIG. 5E shows an illustrative platinum foil (520) which has been micro-machined to form a number of cutouts (530). As discussed above with respect to FIG. 5A, the cutouts (530) form a number of ribbons which are connected by traces. The shape, number, and size of the cutouts determine the geometry of the ribbons. Although the cutouts illustrated in FIG. 5E have uniform size and spacing, the geometry of the cutouts can be altered from frame to frame, or within a single frame to generate the desired ribbon geometries.

The micro-machining process may also include segmenting the platinum foil (520) along the dividing lines (525) to separate platinum foil (520) into platinum frames (500). The dividing lines (525) are illustrated as segmenting the platinum foil (520) into square platinum frames (500). However, for some designs, the platinum frames (500) may have other shapes, including rectangles, parallelograms, rhombuses, trapezoids, triangles, or other shapes.

Figure 6A:
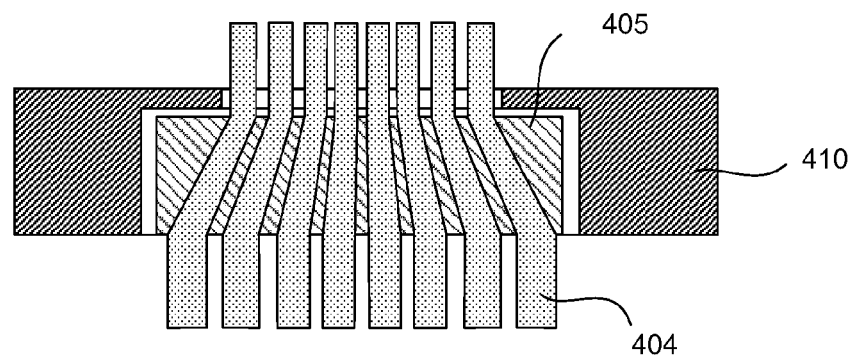
FIGS. 6A-6D are diagrams of various illustrative ribbon via configurations that could be used in a hermetic electrical feedthrough, according to one embodiment of principles described herein.

FIGS. 6A-6D are diagrams of various illustrative ribbon via configurations that could be used in a hermetic electrical feedthrough. The process of micro-machining platinum foil to form ribbons joined by tethers provides the flexibility to make the ribbons in a variety of geometries. FIG. 6A shows ribbons (404) in a fan out configuration. The ribbons (404) in the fan out configuration are more densely packed on one side of the ceramic body (405) and are spaced farther apart on the opposite side of the ceramic body (405). In this configuration, the angle of the individual ribbons (404) within the ceramic body (405) varies between ribbons (404) and the width of the ribbons (404) changes as they pass through the ceramic body (405).

Figure 6B:
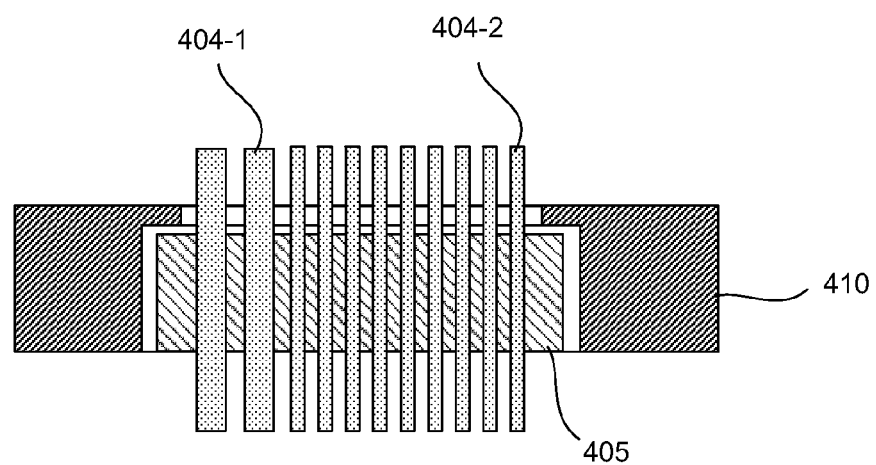

FIG. 6B shows another illustrative embodiment of ribbons passing through the ceramic body (405). In this embodiment, there are a number of thick ribbon vias (404-1) and a number of thin ribbon vias (404-2). The thick ribbon vias (404-1) may be used for applications where a lower electrical resistance or a higher current carrying capability is desired, while the thin ribbon vias (404-2) may be more space efficient in making connections through the ceramic body.

Figure 6C:
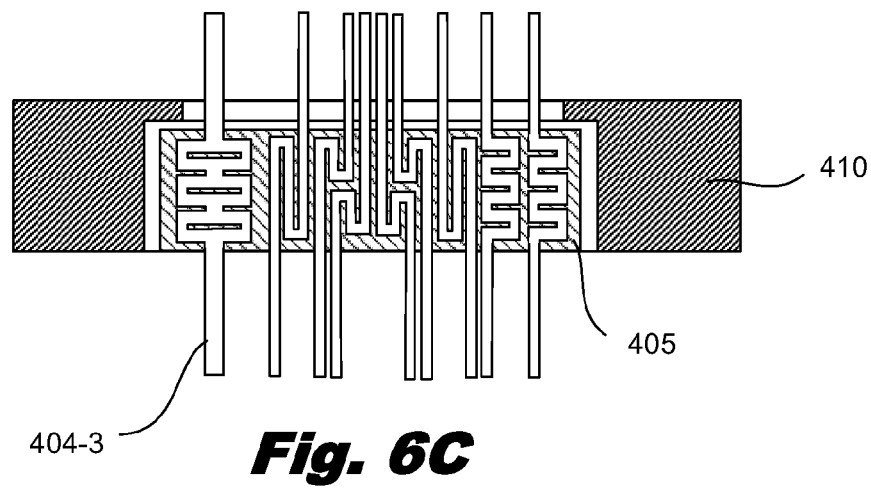

FIG. 6C is a diagram showing a number of illustrative ribbons (404-3) which make one or more turns as they pass through the ceramic body (405). One failure mechanism of a hermetic electrical feedthrough is diffusion of a gas or liquid through a discontinuity or boundary in the feedthrough. For example, a discontinuity occurs between the surface of a ribbon and the surrounding ceramic. These discontinuities tend be more permeable or susceptible to degradation than uniform portions of the feedthrough. One method of decreasing the permeability of a feedthrough is to increase the path length of the discontinuities through the feedthrough. This can be done in a variety of ways, including making the feedthrough thicker or forming ribbons with serpentine paths through the ceramic. In this illustrative embodiment, the diffusion path has been lengthened by forming the ribbons (404-3) in a variety of serpentine shapes. For a gas molecule to travel through the discontinuities between the ceramic (405) and the ribbon (404-3), it must travel along the entire length of the ribbon, including making turns and reversing its course to follow a serpentine ribbon (404-3). Consequently, increasing the length of the ribbon (404-3) can result in a large decrease in the permeability of the feedthrough.

Figure 6D:
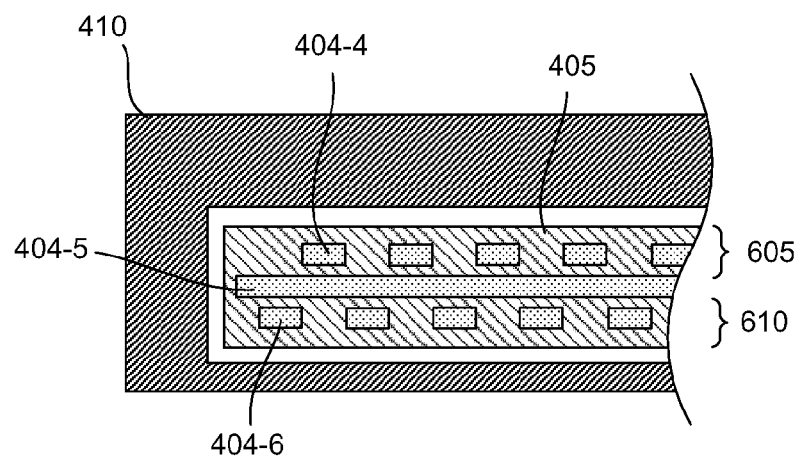

FIG. 6D is a cross-sectional diagram of an illustrative hermetic feedthrough. The cross sectional diagram is taken parallel to the wall of the case (410) and perpendicular to the ribbons (404-4, 404-6). This diagram shows that multiple frames may be embedded in a single ceramic body (405). These multilayer assemblies can be fabricated using additional ceramic and conductive layers. These hermetic feedthrough may include ribbons (404-4, 404-6), ground planes (404-5), or other conductive shapes embedded in the dielectric ceramic body (405). In this illustrative embodiment, in which a first planar group of ribbon vias (404-4) is formed in a first portion (605) of the ceramic body (405) and a second planar group of ribbon vias (404-6) is formed in a second portion (610) of the ceramic body (405). A ground plane (404-5) is formed between the two groups of ribbon vias.

According to one illustrative embodiment, the method of forming a hermetic feedthrough with multiple conductive layers is similar to the method described above for forming a feedthrough with a single conductive layer. The conductive layers are sandwiched between green ceramic sheets and then sintered under pressure to densify the ceramic.

Figure 7:
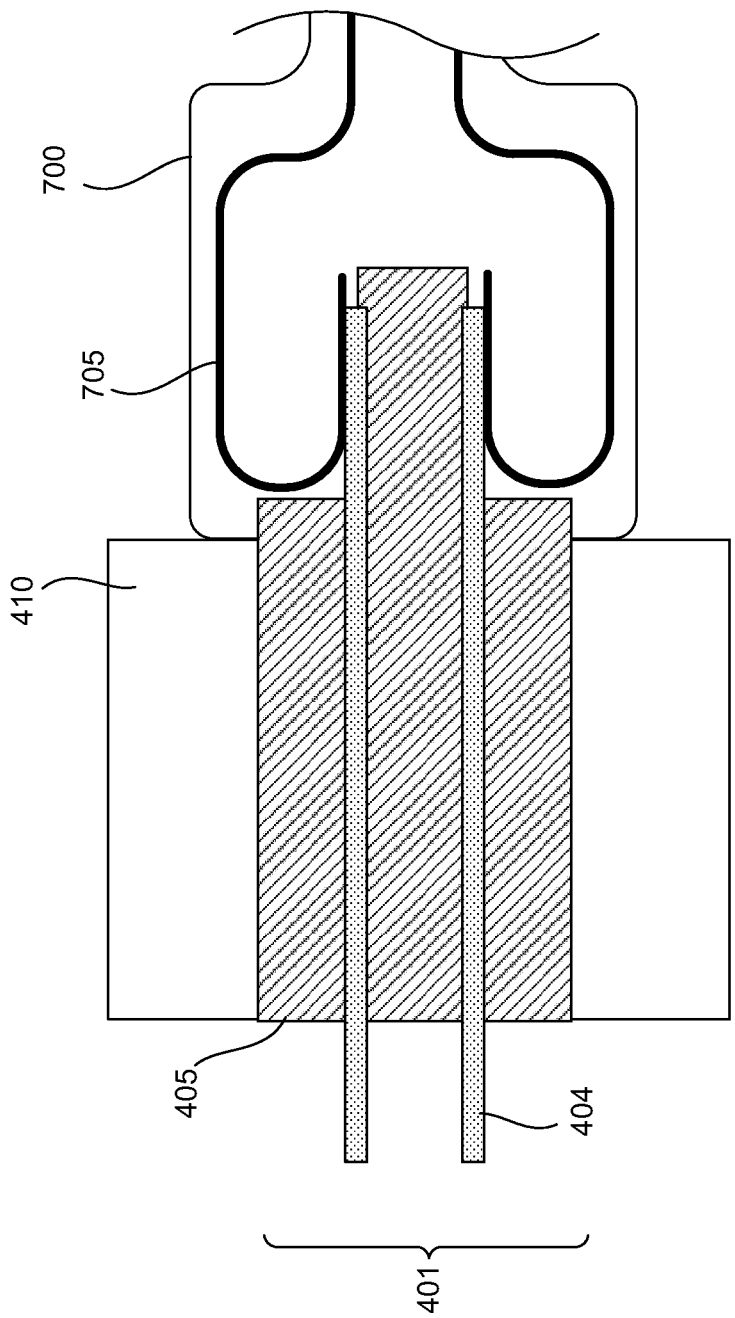
FIG. 7 is a diagram of an illustrative method for connecting to ribbon vias that extend through a hermetic electrical feedthrough, according to one embodiment of principles described herein.

FIG. 7 is a diagram that shows an illustrative hermetic feedthrough (401) joined to a case (410). On the left, the ribbon vias (404) extend out of the feedthrough (401) and are unsupported prior to attachment to the internal circuitry. The ribbon vias (404) pass through the ceramic body (405). On the right, the ribbon vias (404) are supported on one side by a central portion of the ceramic body (405) while being exposed on the opposite side for connection to conductors (705) within the connector (700). In this illustrative embodiment, the conductors (705) may exert a spring force that provides a stable electrical connection with the ribbon vias (404). A variety of other connector types could also be used. Forming a connectorized interface can have a number of advantages, including simplified explant/replacement procedures in which the implanted electronics may be replaced or upgraded without perturbing the electrode placed in the cochlea.

As discussed above, one diffusion path that tends to be more susceptible to gases and liquids is the interface between the ribbon and the ceramic. According to one illustrative embodiment, partial transient liquid phase bonding can be used to improve the seal around the conductive ribbon. Transient liquid phase bonding refers to the process of melting at a eutectic point and subsequently allowing diffusion to alter the composition of the liquid phase causing solidification. After melting, the metal alloy briefly is liquid and flows to fill voids and form a bond with surrounding materials. This change in composition increases the melting point of the liquid, resulting in rapid solidification of the liquid phase. In partial transient liquid phase bonding, the metal structure does not melt through its entire cross section. Instead, at least a portion of the metal remains solid through the entire process, while another portion of the metal melts to form a bond and then resolidifies. Partial transient liquid phase bonding is discussed below and is illustrated in FIGS. 8 and 9A-9D.

Figure 8:
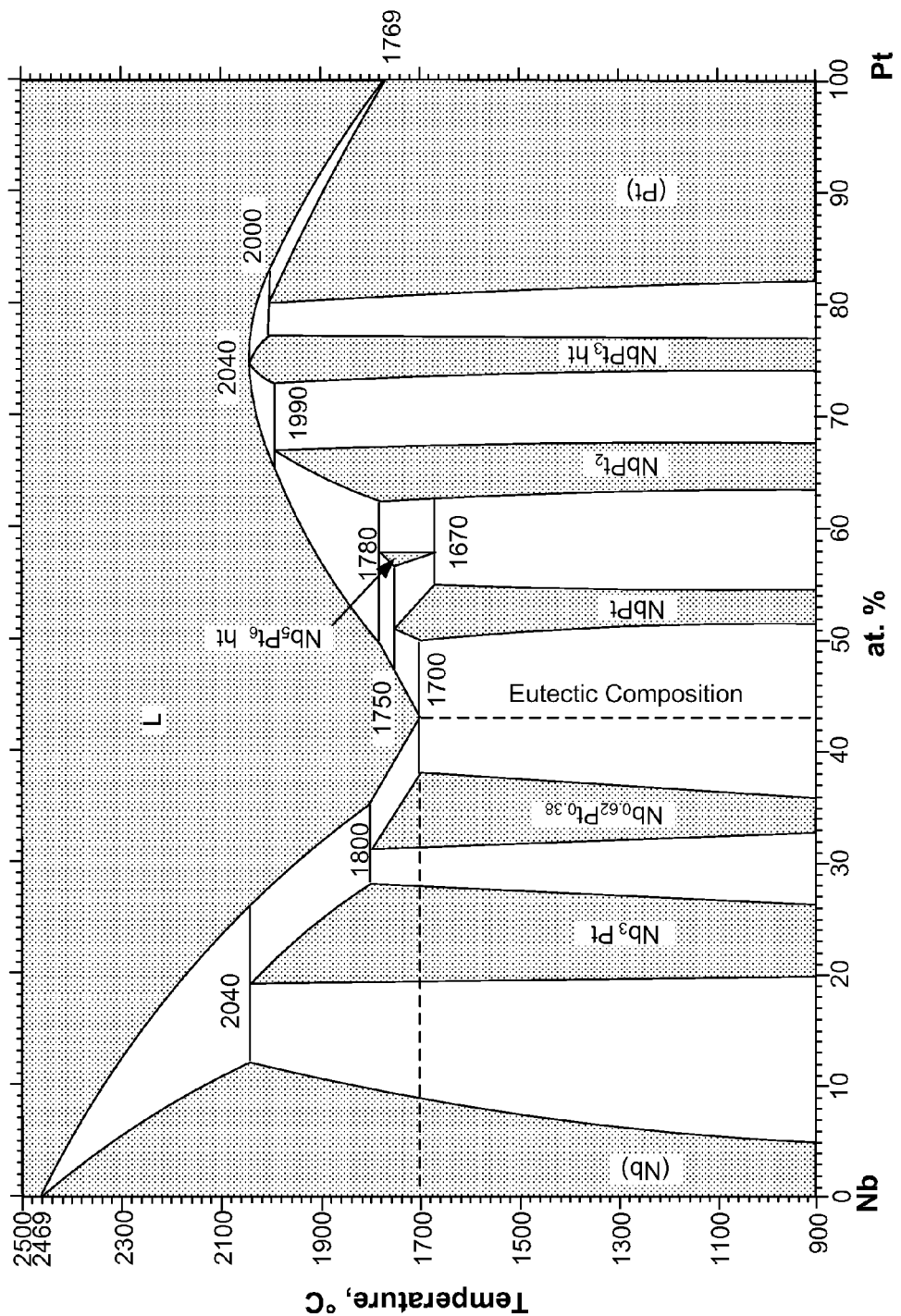
FIG. 8 is an illustrative binary phase diagram for niobium and platinum, according to one embodiment of principles described herein.

FIG. 8 is an illustrative binary phase diagram for niobium and platinum. The diagram in FIG. 8 will be referred to during the later discussion of partial transient liquid phase bonding in the hermetic electrical feedthroughs. The horizontal axis of the chart represents the composition, with a metal that is 100% niobium and 0% platinum being represented on the left and a metal that is 0% niobium and 100% platinum being represented on the right. The other various compositions are listed along the horizontal axis as the percent of platinum in the composition, with the balance being niobium. Various intermetallic compounds are shown as shaded areas with the associated name of the specific compound. The uppermost region, labeled with an "L" represents the temperatures at which specific niobium/platinum alloys are in a liquid state.

The eutectic composition is the specific ratio of the two metals that has a melting point that is lower than any other composition of the two metals. In this illustrative embodiment, the eutectic composition is approximately 43% niobium and 57% platinum. The eutectic temperature is approximately 1700° C., which is the lowest melting temperature of any niobium/platinum composition.

Another characteristic of the niobium/platinum alloy is the relatively high degree of solubility of niobium in platinum.

This is shown by the shaded area to the bottom right of the chart labeled "(Pt)". For compositions with less than 18% niobium, the alloy is a solid solution of niobium in a platinum matrix. This leads to a homogenous composition for the range of platinum/niobium alloys with 18% niobium or less.

Figure 9A:
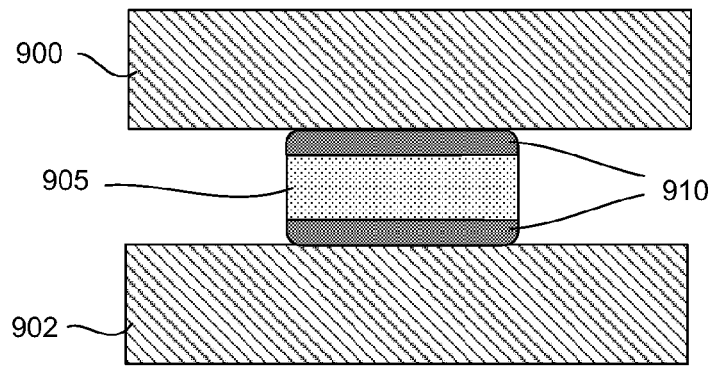
FIGS. 9A-9D are diagrams showing steps in an illustrative partial transient liquid phase bonding method which reduces the permeability of the hermetic feedthrough, according to one embodiment of principles described herein.

FIGS. 9A-9D are cross-sectional diagrams showing illustrative steps in manufacturing a hermetic electrical feedthrough using partial transient liquid phase bonding to decrease the permeability of the feedthrough. FIG. 9A shows a platinum ribbon (905), which has its upper and lower surfaces coated with a niobium layer (910). As discussed above, the niobium layers may be deposited in a number of ways and may be deposited on one or more of the surfaces of the ribbon (905). For example, the niobium (910) may be deposited using chemical vapor deposition on both surfaces of the platinum foil prior to micro-machining the foil into ribbons (905). In other embodiments, the niobium (910) may be deposited after the micro-machining of the platinum foil and may cover the entire perimeter of the ribbons (905). In this embodiment, the niobium layer (910) is substantially pure niobium. However, the niobium layer (910) may be formed from a variety of niobium/platinum alloys which have a niobium composition that is greater than or equal to that of the eutectic composition.

Figure 9B:
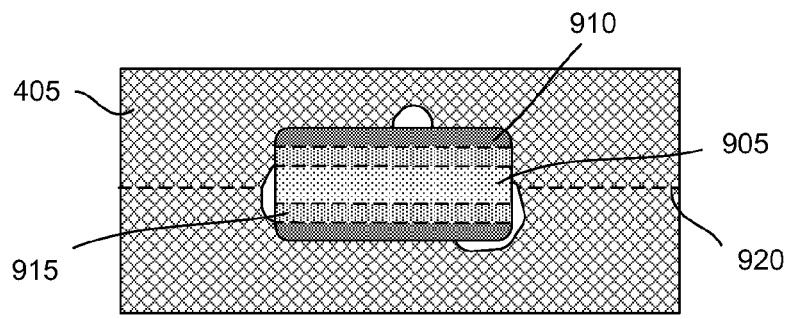

The platinum ribbon (905) is sandwiched between an upper green ceramic tape (900) and a lower green ceramic tape (902). The assembly is then pressed together and sintered at an elevated temperature. This results in the densification and sintering of the green ceramic tapes (900, 902). FIG. 9B shows the platinum ribbon (905) inside the densified ceramic body (405), which is formed from the green ceramic tapes (900, 902; FIG. 9A). According to one illustrative embodiment, the green ceramic tapes (900, 902; FIG. 9A) are formed primarily of alumina with organic binders. During sintering, the temperature of the assembly is raised to approximately 1650 to 1700° C. while mechanical pressure is applied to the assembly. The organic binders are burned out of the two green ceramic tapes (900, 902; FIG. 9A) and the ceramic tapes are fused to form a boundary-less dielectric joint (920). This forms a monolithic densified ceramic body (405). During sintering, the niobium diffuses from the niobium layers (910) into the platinum ribbon (905) to form a diffusion zone (915), which has a range of niobium/platinum compositions, including at least a portion that is at the eutectic composition.

In a next step, the process temperature is raised to at least the eutectic temperature. For example, when a niobium/platinum composition is used, the process temperature may be raised to between 1700 and 1750° C. At this temperature, the portion of the diffusion zone (915) that is at the eutectic composition liquefies. As this portion liquefies, additional niobium and platinum diffuse into the liquid and the liquid portion grows to form a transient liquid phase which flows into voids surrounding the ribbon (905).

Figure 9C:
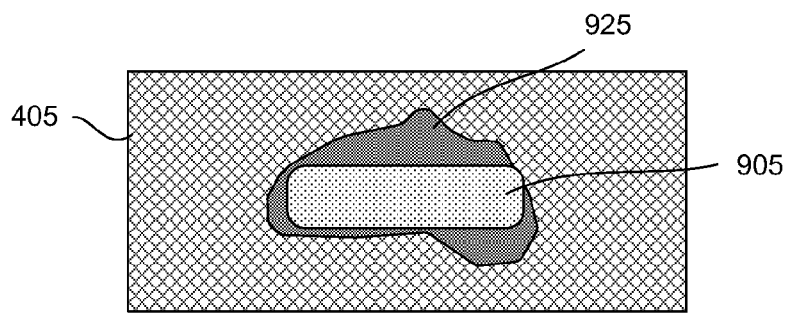

FIG. 9C shows the transient liquid (925) flowing into the asperities surrounding the platinum ribbon (905) and forming a bond between the ceramic body (405) and the platinum ribbon (905). The center portion of the platinum ribbon (905) remains solid. At the eutectic temperature, niobium continues to diffuse out of the transient liquid (925) and into the platinum ribbon (905). This changes the composition of the transient liquid (925) away from the eutectic composition (to the right on the phase diagram in FIG. 8). Consequently, the transient liquid (925) solidifies after briefly being liquid. The transient liquid phase may provide a number of benefits, including wetting the alumina, a reaction bond between with the ceramic, filling in asperities, relieving stresses that may be present in the assembly, and other benefits.

Figure 9D:
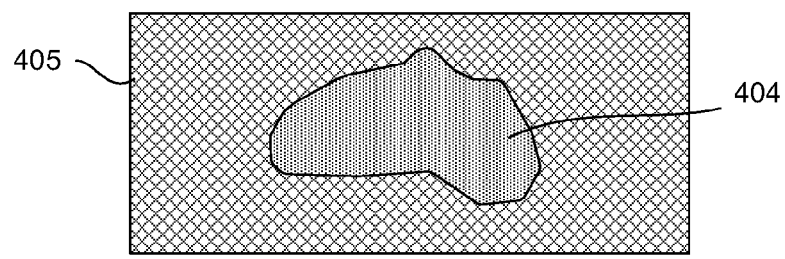

FIG. 9D shows one illustrative embodiment in which the niobium has uniformly diffused into the platinum ribbon to form a solid solution of niobium within the platinum. This results in a substantially uniform alloy composition through the cross-section of the ribbon via (404). As discussed above the solid solubility limit of niobium in platinum is approximately 18% niobium. Consequently, to achieve a substantially uniform solid solution of niobium in platinum the overall ratio of niobium to platinum is less than or equal to approximately 18% niobium. This alloy (404) forms a conductive path through ceramic body (405) with reduced permeability.

Figure 10:
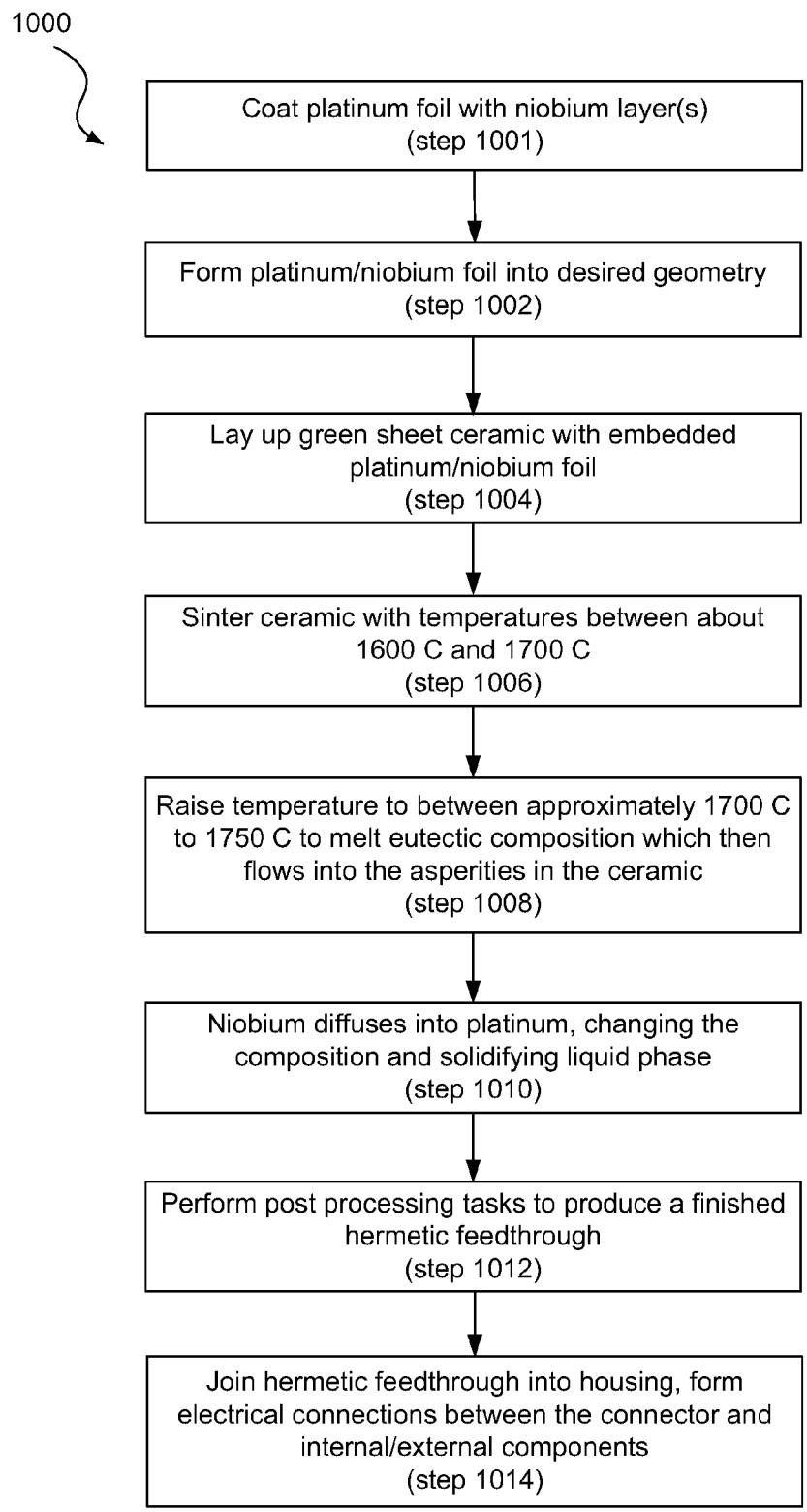
FIG. 10 is a flowchart showing an illustrative method for manufacturing a hermetic feedthrough using partial transient liquid phase bonding, according to one embodiment of principles described herein.

FIG. 10 is a flowchart showing an illustrative method for manufacturing a hermetic feedthrough using partial transient liquid phase bonding. The steps described below can be altered in sequence or replaced by alternative steps. In a first step, a sheet of platinum foil is coated with one or more niobium layers (step 1001). According to one illustrative embodiment, the sheet may be large enough to form a plurality of frames. The niobium layer could be patterned such that niobium is deposited over only a portion of the sheet. Alternatively, a niobium layer can be formed using niobium foil that is joined to the platinum foil. The platinum foil and niobium layer are formed into a frame having the desired geometry (step 1002). As discussed above, the platinum foil may have a variety of geometries, including a plurality of ribbons connected by tethers. Where a large sheet of platinum foil is used, a micro-machining process may be used to create cutouts into the platinum foil to form ribbons connected by tethers. The large sheet may then be segmented into a plurality of frames. As discussed above, each frame may comprise a plurality of ribbons connected tethers.

The platinum/niobium frame is then sandwiched between green ceramic tapes (step 1004). This assembly is then sintered under pressure and at temperatures between about 1600 to 1700° C. (step 1006). This step in the process is called "inclusion sintering" because the conductor is included in the ceramic during sintering. During inclusion sintering there are a number of factors that can be considered, including the shrinkage of the ceramic, burn out of organic binders, flow of ceramic material under pressure, the relative bonding that takes place between the embedded conductor and the surrounding ceramic, and other considerations. The considerations can influence various processing parameters, such as the process temperature, the geometry of the individual components within the assembly, the type of atmosphere (inert, vacuum, or reactive) in which the sintering takes place, and other parameters.

The process temperature is then raised to between approximately 1700 to 1750° C. to melt the eutectic composition which then flows into asperities and forms a bond with the surrounding ceramic (step 1008). These asperities may include grain boundaries between ceramic regions, voids between the ribbon via and the ceramic, and other discontinuities.

At this elevated temperature, the niobium diffuses into platinum, which changes the composition and solidifies the liquid phase (step 1010). A number of post processing tasks may be performed to produce a finished hermetic feedthrough (step 1012). For example, the post processing tasks may include the removal of the tethers to separate the frame into individual ribbons. The hermetic connector is then joined into the case and electrical connections between the hermetic connectors and internal/external components (step 1014). As discussed above, the hermetic feedthrough may be joined to the case in a variety of ways, including brazing, active metal brazing, ceramic/glass/metal bonding, transient liquid phase bonding, or other techniques. In some embodiments, the hermetic feedthroughs may be joined to a separate flange that is then laser welded to the titanium case.

Throughout the specification and figures, niobium has been used as an illustrative alloying element, which may be used in combination with platinum to form a partial liquid transient phase bond. A variety of the materials may be used to form the partial liquid transient phase bond. By way of example and not limitation, the alloying element or compound may be tantalum, nickel, copper, or other suitable material. It is desirable that the combination of the alloying element and the platinum have one or more of the following characteristics. First, the eutectic composition of the alloying element and platinum should have a eutectic temperature that is below the melting temperature the core or platinum ribbon. Second, the alloying element or compound may have a high solubility in platinum. Third, the combination of the alloying element and platinum may have excellent chemical stability and biocompatibility. Fourth, the combination of the alloying element and platinum may have low electrical resistance. These and other characteristics can serve as touch points for selecting a particular alloying element and matrix metal for a particular combination. Hermetic feedthroughs formed using the method and principles described above may be used in a variety of applications, including applications outside of the field of implanted medical devices. For example, the hermetic feedthroughs may be used in high vacuum systems, high temperature applications, aggressive chemical environments, space systems, or other environments. In some of these applications, other matrix metals may be used in place of platinum.

In sum, the feedthroughs described above may be combined with the case to produce a superior hermetic enclosure with reduced height and increased reliability. Partial transient liquid phase bonding is a flexible process which improves the bonding between a conductive via and surrounding ceramic. For example, the composition can be varied to yield different amounts of liquid. The alloy system can be modified to change the eutectic melting temperature. The ribbon vias may be coated with the alloying material to select where the liquid forms.

The preceding description has been presented only to illustrate and describe embodiments and examples of the principles described. This description is not intended to be exhaustive or to limit these principles to any precise form disclosed. Many modifications and variations are possible in light of the above teaching.

What is claimed is:

1. An electrical feedthrough comprising:
   a ceramic body; and
   ribbon vias extending through the ceramic body, the ribbon vias extending out of at least one surface of the ceramic body, wherein a width of the ribbon vias vary through a thickness of the ceramic body, wherein the ribbon vias comprise a fan out configuration with ribbon vias spaced more densely on one side of the ceramic body and spaced farther apart on an opposite side of the ceramic body.

2. The feedthrough of claim 1, in which the ribbon vias comprise platinum.

3. The feedthrough of claim 2, in which the ribbon vias further comprise a niobium layer disposed over said platinum.

4. The feedthrough of claim 1, in which voids surrounding the ribbon vias are filled by a transient liquid phase comprising an alloy of platinum and niobium.

5. The feedthrough of claim 1, in which the ceramic body is formed from green ceramic sheets.

6. The feedthrough of claim 5, in which a diffusion zone between niobium and platinum is formed during inclusion sintering of the green ceramic sheets.

7. The feedthrough of claim 1, in which the ribbon vias are formed from a platinum foil having a thickness of 100 microns or less, a niobium layer being deposited on at least one surface of the platinum foil.

8. The feedthrough of claim 1, in which the feedthrough is less than 2.5 mm in height, the feedthrough being brazed into an aperture in a hermetic case.

9. The feedthrough of claim 1, in which the ribbon vias form serpentine conduction paths through the ceramic body.

10. The feedthrough of claim 1, in which a first planar group of ribbon vias is formed in a first portion of the ceramic body and a second planar group of ribbon vias is formed in a second portion of the ceramic body.

11. The feedthrough of claim 1, wherein the ribbon vias extend out of both sides of the ceramic body.

12. The feedthrough of claim 2, wherein the ribbon vias further comprise a tantalum layer disposed over said platinum, in which the partial transient liquid phase bond comprises an alloy of tantalum and platinum.

13. The feedthrough of claim 6, wherein at least a portion of the diffusion zone comprises a eutectic composition of platinum and niobium.

14. The feedthrough of claim 13, further comprising a hypereutectic composition of platinum and niobium filling voids surrounding the ribbon vias.

15. The feedthrough of claim 1, wherein:
   a first planar group of ribbon vias is formed in a left portion of the ceramic body, the first group comprising serpentine vias each comprising a shape with at least one right turn and at least one left turn; and
   a second planar group of ribbon vias is formed in a right portion of the ceramic body, the second group comprising serpentine vias each comprising a shape with at least one right turn and at least one left turn.

16. The feedthrough of claim 15, wherein the serpentine vias comprise a diffusion path length at an interface between the ribbon vias and ceramic body, the diffusion path length being greater than a thickness of the ceramic body.

17. The feedthrough of claim 1, further comprising a ground plane embedded in the ceramic body and underlying the ribbon vias.

18. The feedthrough of claim 17, further comprising an additional conductive layer comprising ribbon vias underlying the ground plane.

19. The feedthrough of claim 9, in which a first planar group of ribbon vias is formed in a first portion of the ceramic body and a second planar group of ribbon vias is formed in a second portion of the ceramic body.

20. The feedthrough of claim 10, wherein a first planar group of ribbon vias is formed in a first left hand portion of the ceramic body and a second planar group of ribbon vias is formed in a second right hand portion of the ceramic body.

21. An electrical feedthrough assembly comprising:
   a ceramic body; and
   a plurality of ribbon vias extending through the ceramic body, the plurality of ribbon vias comprising a micromachined platinum foil having a thickness of less than 100 microns and plated with a layer of niobium such that when the ceramic body and plurality of ribbon vias are heated above a eutectic point, interfaces between the plurality of ribbon vias and the ceramic body are sealed by a partial transient liquid phase bond such that voids surrounding the plurality of ribbon vias are filled by an alloy of platinum and niobium, in which the plurality of ribbon vias extend out of two sides of the ceramic body and are configured to make electrical connections through the ceramic body between an internal electrical device and an external electrical device.

22. An electrical feedthrough comprising:

a ceramic body; and ribbon vias extending through the ceramic body and extending out of at least one surface of the ceramic body, wherein a width of the ribbon vias vary through a thickness of the ceramic body, wherein the ribbon vias comprise:

a first planar group of ribbon vias is formed in a left portion of the ceramic body, the first group comprising serpentine vias with a right turn and a left turn; and a second planar group of ribbon vias is formed in a right portion of the ceramic body, the second group comprising serpentine vias with a right turn and a left turn;

wherein the serpentine vias comprise a diffusion path length at an interface between the vias and ceramic body, the diffusion path length being greater than a thickness of the ceramic body.

23. An electrical feedthrough comprising:

a ceramic body; and a ribbon via extending through the ceramic body, an interface between the ribbon via and the ceramic body comprising a partial transient liquid phase bond, the ribbon via extending out of at least one surface of the ceramic body, wherein a width of the ribbon via varies through a thickness of the ceramic body; and a ground plane embedded in the ceramic body and underlying the ribbon via.

* * * * *